United States Patent [19]

Xiu

[11] Patent Number: 5,547,672
[45] Date of Patent: Aug. 20, 1996

[54] ACCELERATED WOUND HEALING

[76] Inventor: Rui-Juan Xiu, Fatburs Kvarngatan 3 6 tr/43, Stockholm, Sweden

[21] Appl. No.: 162,059
[22] PCT Filed: Jun. 20, 1991
[86] PCT No.: PCT/SE91/00451
   § 371 Date: Jan. 18, 1994
   § 102(e) Date: Jan. 18, 1994
[87] PCT Pub. No.: WO93/00104
   PCT Pub. Date: Jan. 7, 1993
[51] Int. Cl.$^6$ .................................................. A61K 35/78
[52] U.S. Cl. ........................ 424/195.1; 514/783; 514/866
[58] Field of Search ........................ 424/195.1; 514/866, 514/783

[56] References Cited

FOREIGN PATENT DOCUMENTS 59-152319  8/1984  Japan.

OTHER PUBLICATIONS

Ukai et al. *Chem. Pharm. Bull.*, vol. 26(6), pp. 1707–1712, (1978).
Liu et al. *Zhonghua Fangshe Yixue Yu Fangh Zazhi*, vol. 5(4), pp. 262–265, (1985). (Abstract only).
Huiping et al. *J. China Pharm. Univ.*, vol. 20(5), pp. 303–305, (1989).
Xue et al. *J. China Pharm. Univ.*, vol. 20(3), pp. 181–183, (1989).
Jianhe et al. *J. China Pharm. Univ.*, vol. 20(6), pp. 344–347, (1989).
Sheng et al. *J. China Pharm. Univ.*, vol. 21(1), pp. 39–42, (1990).
Dorland's Pocket Medical Dictionary (24th Edition), W. B. Saunders Co., p. 601, (1989).
Chemical Abstracts, vol. 111, No. 23, 4 Dec. 1989, (Columbus, Ohio, US), Xia, Erning et al.: "Isolation, analysis, and biological activities of the polysaccharide of Tremella fuciformis Berkeley", see p. 347, abstract 211950h, & Zhenjun Xuebao 1988, 7 (3), 166–174.
Dialog Information Services, WPIL 351, accession no. 007619454, Yg Nonogawa Shoji; "Antiinflammatory prepn.—contains active substance extracted from fruiting body or mycelium of heterobasidiae", & JP 6318537 A 880728 8836 (Basic).
Chemical Abstracts, vol. 111, No. 15, 9 Oct. 1989, (Columbus, Ohio, US), Xue, Weijian et al.: "Prevention and treatment of alloxan–induced diabetes in mice by polysaccharides isolated from Tremella fuciformis and Auricularia auricula", see p. 51, abstract 126794r, & Zhongguo Yaoke Daxue Xuebao 1989, 20 (3), 181–183.

*Primary Examiner*—Douglas W. Robinson
*Assistant Examiner*—Howard C. Lee
*Attorney, Agent, or Firm*—Merchant, Gould, Smith, Edell, Welter & Schmidt

[57] ABSTRACT

Use of extracts of *Tremella fuciformis* (Berk) in the manufacture of a pharmaceutical agent for treatment of wounds and other skin injuries.

4 Claims, No Drawings

ACCELERATED WOUND HEALING

The present invention refers to agents containing extracts of a fungus, *Tremella fuciformis* (Berk), which is a non-toxic, nutritional remedy, which have a potential stimulating effect on cell growth.

The fungus *Tremella fuciformis* (Berk), referred to as TFB, belongs to the class Hymenomycetes, in the division Eumycota (Ainsworth & Bisby's "Dictionary of the Fungi", 1971).

In Chinese traditional medicine, *Tremella fuciformis* (Berk) has long had a reputation of being a general nutritional remedy. Thus, in ancient medical literature *Tremella fuciformis* has been ascribed curative properties such as promoting saliva secretion, moistening lungs and stopping dry cough, decreasing itching in the throat, inhibiting cough with blood, relieving stomach pain, stopping constipation of blood in the stool, recovering tired muscles, supporting good spirits and memory, keeping skin young and hair shiny, restoring vitality etc.

During the last 15–20 years scientific studies on the various effects of *Tremella fuciformis* have been carried out in China and Japan. The anti-inflammatory effect of polysaccharides from fruiting bodies of several fungi has been studied by Ukai et al. (J. Pharmacobiodyn., 6(12):983–90, 1983). Assays were performed on the carrageenan induced edema and scald-induced hyperalgesia in the hindpaw of rats. Among the crude polysaccharides studied, those obtained from *Tremella fuciformis* was found to be ineffective in inhibiting scald-induced hyperalgesia. Furthermore, the mechanism of the anti-inflammatory activity of the polysaccharides remained obscure.

A thermal injury of the skin is followed by a rapid development of massive edema and the exudate contains very high concentrations of plasma proteins. Until today, the mechanism of this condition is not well understood. During the development of edema the volume of the circulating plasma is significantly decreased (hypovalemia), which often causes development of a circulatory shock. Thus, there exists a need for increasing the plasma flow by improving the permeability of the microvessels or inhibiting the exudate to obstruct the hypovalemia.

It is the object of this invention to make available a pharmaceutical agent which can be used for the treatment of wounds and for the treatment of other tissue injuries.

The preparation of TFB paste was performed as follows. *Tremella fuciformis* (Berk) as a dried powder (product of the Fu Jian province, China) was added in 10 g to 600 ml bi-distilled water and heated with stirring until boiling. The boiling was continued for 20 minutes during which the suspension turned to a white paste. The paste was then autoclaved at 120° C. for 15 min before use.

White male rabbits (pure New Zealand species) of 2–3 kg body weight were used throughout. The animals were shaved at the back of the ears and on the back of the body on both sides of the spinal column with an area of 12×44 $cm^2$. Balance weights of stainless steel were used for causing wounds. The weights used were of 25 and 50 g with an engagement area of 1 and 3.14 $cm^2$, respectively. They were boiled in water cooled to 40° C., 50° C. and 60° C., respectively, and then applied with one spot on each ear and two spots on each side of the back of the animal for one minute without additional pressure.

The burned spots on the right side of the spinal column were treated with TFB paste and the burned spots on the left side were treated with standard physiological saline. Three groups of two rabbits were studied. The first group (R1 and R2) received 25 g weights of 50° C., the second (R3 and R4) 50 g weights of 40° C. and the third (R5 and R6) 50 g weights of 60° C. All the procedures were performed under aseptic conditions.

Sterilized TFB paste was applied to the wound immediately after burning and covered with a sterile tissue. The control spots were covered with sterile saline impregnated tissues. The treatment was repeated once a day until the wounds were healed.

The wound healing was estimated according to the following parameters:

1. Wound area ($cm^2$).
2. Degree of exudation.
3. Healing time.

The wound area and hyperemia around the wound spots were measured 24, 48 and 72 hours after burning. The results of wound healing are shown in Table 1 after burning an area of 1 $cm^2$ at 50° C. and in Table 2 after burning an area of 3.14 $cm^2$ at 40° and 60° C.

In all cases the TFB significantly reduced the area and the hyperemia of the wounds after the second day of treatment. After burning at a temperature of 60° C., the exudation in the control group was quite obvious in 4 out of 6 wounds, but in the corresponding wounds treated with TFB paste only 2 out of 6 wounds showed a light exudation (Table 2). When the burning of an 1 $cm^2$ area was performed at a temperature of 50° C. the time needed for healing was 4–8 days in the group treated with TFB but 10–15 days in the control group. When the burning of an 3.14 $cm^2$ area was performed at a temperature of 40° C. the time needed for healing was 10–14 days in the group treated with TFB but 16–20 days in the control group (Table 2). When the corresponding wounds were created at 60° C., the time needed for healing was 13–16 days for the group treated with TFB and 17–21 days for the control group. TFB thus markedly accelerated the wound healing process.

TFB also exhibited a softening effect on the scab of the wounds. All the wounds were covered with scabs on the 3–4th day in group 1 and on the 6–8th day in group 2 and 3. However, the wounds and the skin around them were much lesser and softer when treated with TFB than in the control groups. After burning a 3.14 $cm^2$ wound at 60° C. and treating it with TFB, the wound has 28 hours later a peripheral border and no scab on it. The swelling and the hyperemia is very light and the skin around the wound is softened by TFB. Corresponding wounds only treated with saline have a hard scab and the skin around the wounds has significant hyperemia and swelling.

As the TFB paste is non-toxic for human beings, an excess amount of the extract in treating a person will be harmless to the patient. The extract of *Tremella fuciformis* (Berk) is according to the invention applied to a wound as a paste by smearing but other forms of application, as an aerosol which is sprayed or a solution which is painted, can also be used.

TABLE 1

Effect of TFB on wound healing (1 cm² burned area).

| Rabbit | Wound area (cm²)* | | | | | | Exudation | | Time of recovery (d) | | Burning temp. (C) |
|---|---|---|---|---|---|---|---|---|---|---|---|
| | 24 h | | 48 h | | 72 h | | | | | | |
| | Cont. | Trea. | Cont. | Trea. | Cont. | Trea. | Cont. | Trea. | Cont. | Trea. | |
| R1 (A) | 3.00 | 2.00 | 2.80 | 2.00 | 2.50 | 1.80 | − | − | 15 | 8 | 50 |
| R1 (B) | 2.50 | 2.10 | 2.50 | 1.60 | 2.00 | 1.40 | − | − | 10 | 4 | 50 |
| R1 (C) | 3.00 | 2.10 | 2.80 | 1.60 | 2.40 | 1.50 | − | − | 11 | 6 | 50 |
| R2 (A) | 3.10 | 1.90 | 3.10 | 2.00 | 2.80 | 1.70 | + | − | 13 | 8 | 50 |
| R2 (B) | 2.00 | 1.80 | 1.80 | 1.50 | 1.80 | 1.40 | − | − | 10 | 5 | 50 |
| R2 (C) | 2.70 | 2.00 | 2.50 | 1.50 | 2.00 | 1.30 | − | − | 12 | 6 | 50 |

(A) Wound spots on both ears.
(B) Wound spots on both sides of the body, upper part.
(C) Wound spots on both sides of the body, lower part.
*The wound area was measured by width × length.

TABLE 2

Effect of TFB on wound healing (3.14 cm² burned area).

| Rabbit | Wound area (cm²)* | | | | | | Exudation | | Time of recovery (d) | | Burning temp. (C) |
|---|---|---|---|---|---|---|---|---|---|---|---|
| | 24 h | | 48 h | | 72 h | | | | | | |
| | Cont. | Trea. | Cont. | Trea. | Cont. | Trea. | Cont. | Trea. | Cont. | Trea. | |
| R3 (A) | 5.47 | 4.91 | 5.30 | 2.89 | 5.30 | 2.89 | − | − | 19 | 14 | 40 |
| R3 (B) | 5.71 | 3.80 | 5.30 | 3.46 | 4.80 | 3.14 | − | − | 17 | 10 | 40 |
| R3 (C) | 5.72 | 4.41 | 4.90 | 3.80 | 4.52 | 3.60 | − | − | 20 | 12 | 40 |
| R4 (A) | 4.92 | 4.22 | 5.20 | 3.91 | 5.30 | 3.74 | − | − | 18 | 14 | 40 |
| R4 (B) | 5.30 | 5.10 | 5.32 | 4.82 | 5.14 | 3.90 | − | − | 16 | 13 | 40 |
| R4 (C) | 5.42 | 4.91 | 5.10 | 4.91 | 5.10 | 3.24 | − | − | 17 | 10 | 40 |
| R5 (A) | 6.15 | 5.06 | 4.91 | 3.60 | 4.97 | 3.66 | ++ | + | Necrosis on the 9th day | 16 | 60 |
| R5 (B) | 6.07 | 5.16 | 5.80 | 3.80 | 5.50 | 3.56 | − | − | 18 | 14 | 60 |
| R5 (C) | 6.00 | 5.30 | 5.80 | 3.80 | 5.86 | 3.90 | ++ | − | 17 | 13 | 60 |
| R6 (A) | 5.91 | 5.30 | 5.80 | 5.10 | 5.20 | 3.40 | ++ | + | 21 | 15 | 60 |
| R6 (B) | 6.20 | 5.90 | 6.00 | 4.80 | 5.80 | 3.60 | + | − | 18 | 14 | 60 |
| R6 (C) | 6.10 | 5.90 | 6.20 | 4.00 | 5.30 | 3.66 | − | − | 17 | 15 | 60 |

Legends as in Table 1.

I claim:

1. A method for treating a skin injury comprising applying to the injury a pharmaceutical agent consisting essentially of a paste of *Tremella fuciformis* (Berk).

2. The method of claim 1, wherein the paste of *Tremella fuciformis* (Berk) is in a pharmaceutically acceptable carrier.

3. The method of claim 2, wherein the pharmaceutically acceptable carrier is water.

4. The method of claim 1, wherein the skin injury is a wound.

* * * * *